United States Patent
Kudo et al.

(10) Patent No.: US 9,989,450 B2
(45) Date of Patent: Jun. 5, 2018

(54) EROSION TEST APPARATUS, ACCELERATOR AND EROSION TEST METHOD

(71) Applicant: MITSUBISHI HITACHI POWER SYSTEMS, LTD., Kanagawa-ken (JP)

(72) Inventors: Daisuke Kudo, Tokyo (JP); Taiji Torigoe, Tokyo (JP); Junichiro Masada, Yokohama (JP); Koji Takahashi, Yokohama (JP); Yoshitaka Uemura, Yokohama (JP); Yoshifumi Okajima, Tokyo (JP); Naotoshi Okaya, Yokohama (JP); Eisaku Ito, Tokyo (JP); Masahiko Mega, Tokyo (JP); Shigenari Horie, Tokyo (JP); Shuji Tanigawa, Tokyo (JP); Yasuhiko Tsuru, Tokyo (JP); Keizo Tsukagoshi, Yokohama (JP); Masamitsu Kuwabara, Yokohama (JP)

(73) Assignee: MITSUBISHI HITACHI POWER SYSTEMS, LTD., Kanagawa-Ken (JP)

( * ) Notice: Subject to any disclaimer, the term of this patent is extended or adjusted under 35 U.S.C. 154(b) by 113 days.

(21) Appl. No.: 14/933,373

(22) Filed: Nov. 5, 2015

(65) Prior Publication Data
US 2016/0131570 A1    May 12, 2016

(30) Foreign Application Priority Data

Nov. 11, 2014    (JP) .................................. 2014-228813

(51) Int. Cl.
*G01N 3/56*    (2006.01)
*G01N 17/00*    (2006.01)

(52) U.S. Cl.
CPC ............... *G01N 3/565* (2013.01); *G01N 3/56* (2013.01); *G01N 3/567* (2013.01); *G01N 17/00* (2013.01)

(58) Field of Classification Search
CPC ........... G01N 3/56; G01N 3/565; G01N 3/567
See application file for complete search history.

(56) References Cited

U.S. PATENT DOCUMENTS

| 5,356,672 A | * | 10/1994 | Schmitt, III | .......... C23C 16/452 118/723 ME |
| 2013/0306154 A1 | * | 11/2013 | Moliere | .................... F17D 3/00 137/1 |
| 2015/0226611 A1 | * | 8/2015 | Busche | ............... H01L 21/6833 374/121 |

FOREIGN PATENT DOCUMENTS

| JP | 62-97941 | 6/1987 |
| JP | 63-6341 | 1/1988 |

(Continued)

OTHER PUBLICATIONS

M. Kirschner et al., "Erosion Testing of Thermal Barrier Coatings in a High Enthalpy Wind Tunnel", Proceedings of ASME Turbo Expo 2014:Turbine Technical Conference and Exposition GT2014-25523, Jun. 16-20, 2014, Düsseldorf, Germany, pp. 1-12.

*Primary Examiner* — Paul West
(74) *Attorney, Agent, or Firm* — Wenderoth, Lind & Ponack, L.L.P.

(57) ABSTRACT

An erosion test apparatus includes a combustor configured to obtain a combustion gas by mixing and combusting compressed air and a fuel, and an erodent supply unit configured to supply an erodent to the combustion gas. The erosion test apparatus further includes an accommodation support unit configured to accommodate and support a test piece having a front surface coated through thermal barrier coating, and an accelerator configured to accelerate the (Continued)

combustion gas including the erodent to collide with the test piece.

6 Claims, 5 Drawing Sheets

(56) References Cited

FOREIGN PATENT DOCUMENTS

| | | |
|---|---|---|
| JP | 64-6840 | 1/1989 |
| JP | 8-62114 | 3/1996 |
| JP | 2723381 | 3/1998 |
| JP | 2005-232590 | 9/2005 |
| JP | 2007-507604 | 3/2007 |
| WO | 2005/056879 | 6/2005 |

* cited by examiner

EROSION TEST APPARATUS, ACCELERATOR AND EROSION TEST METHOD

BACKGROUND OF THE INVENTION

Field of the Invention

The present invention relates to an erosion test apparatus, an accelerator and an erosion test method.

Priority is claimed from Japanese Patent Application No. 2014-228813, filed Nov. 11, 2014, the content of which is incorporated herein by reference.

Description of Related Art

For the purpose of improving efficiency of a gas turbine, a temperature of a gas to be used may be set to a high value. That is, turbine members (a turbine blade, a turbine vane, and so on) of the gas turbine are exposed to a high temperature gas. For this reason, thermal barrier coating (TBC) is performed on surfaces of the turbine members. The thermal barrier coating is formed by thermally spraying a flame coating material such as a ceramic-based material having low thermal conductivity onto the surface of the turbine member serving as a flame coating target. As the turbine member is coated by the above-mentioned thermal barrier coating, thermal insulation properties and durability of the turbine member are improved.

The thickness of the thermal barrier coating decreases due to erosion caused by various particulates contained in a combustion gas.

In Japanese Unexamined Patent Application, First Publication No. 2005-232590, a technology of improving erosion resistance of the thermal barrier coating while low thermal conductivity is maintained is disclosed. Specifically, as the thermal barrier coating, a technology of providing a c/a ratio of a zirconia lattice of a range of about 1.0117 to about 1.0148, including a zirconia-containing ceramic composition stabilized in a tetragonal crystal form using a metal oxide stabilizer of a quantity of stabilization instead of only yttria, and having porosity of about 0.1 to 0.25 is proposed.

In the above-mentioned thermal barrier coating, in order to confirm the above-mentioned erosion resistance, an evaluation test using a test piece may be performed.

In Japanese Unexamined Patent Application, First Publication No. H08-062114 (hereinafter "JP H08-062114"), in a test apparatus for sandblasting a test piece with a powder conveyed by a carrier gas and measuring abrasion loss of the test piece, a technology of heating the carrier gas to a desired temperature to perform the sandblasting is proposed.

In the above-mentioned test apparatus disclosed in JP H08-062114, the carrier gas can be heated to about 800° C. that is approximate to a melting temperature of a base material of the test piece. However, the carrier gas cannot be heated to a temperature that exceeds the melting temperature of the base material. This is because a heat exchanger is used as a carrier gas heating unit. In the test apparatus disclosed in JP H08-062114, since a gas cylinder is used as a supply source of the carrier gas, a flow velocity of the carrier gas cannot be sufficiently increased.

For this reason, for example, when the thermal barrier coating of a high output type gas turbine using a combustion gas having a high flow velocity at a temperature of about 1500° C. is tested, since the thermal barrier coating cannot be performed under the same boundary condition as a real machine, erosion resistance of the thermal barrier coating may not be properly evaluated.

In order to obtain a combustion gas having a high temperature and a high flow velocity, while use of a combustor of a real machine may be considered, the apparatus would increase in size.

SUMMARY OF THE INVENTION

The present invention is directed to provide an erosion test apparatus, an accelerator and an erosion test method that are capable of properly evaluating erosion resistance of thermal barrier coating of a test piece while suppressing an increase in size of the apparatus.

According to a first aspect of the present invention, an erosion test apparatus includes a combustor configured to mix and combust compressed air and a fuel to obtain a combustion gas; and an erodent supply unit configured to supply an erodent to the combustion gas. The erosion test apparatus further includes an accommodation support unit configured to accommodate and support a test piece having a front surface coated through thermal barrier coating; and an accelerator configured to accelerate the combustion gas including the erodent to collide with the test piece.

According to the above-mentioned configuration, the combustion gas of the combustor can be used as a carrier gas of the erodent. For this reason, the temperature of the test piece is heated to the same temperature as the turbine member of the real machine. Further, the combustion gas including the erodent and combusted by the combustor can be accelerated by the accelerator and then collide with the test piece. Accordingly, the flow velocity of the combustion gas can be increased to the same flow velocity as the combustion gas of the real machine using the compact combustor. That is, the boundary condition of the thermal barrier coating of the test piece can be the same as the boundary condition of the thermal barrier coating in the real machine.

As a result, the erosion resistance of the thermal barrier coating of the test piece can be properly evaluated while suppressing an increase in size.

According to a second aspect of the present invention, the erosion test apparatus of the first aspect may include a cooling unit configured to blow a coolant to a back surface of the test piece to cool the test piece.

According to the above-mentioned configuration, the base material of the test piece coated through the thermal barrier coating can be cooled. For this reason, the same temperature distribution as the temperature distribution in the thickness direction of the turbine member of the real machine can be produced in the test piece.

According to a third aspect of the present invention, in the erosion test apparatus, the accelerator according to the first or second aspect may be connected to the combustor. Further, the erosion test apparatus may include a throttling section and a straight pipe section. The throttling section is formed in a tubular shape having a flow path cross-sectional area that gradually reduces downstream in a direction in which the combustion gas flows. The straight pipe section is formed in a straight pipe shape having a constant flow path cross-sectional area.

In this way, as the flow path cross-sectional area of the throttling section is gradually reduced, the flow velocity of the combustion gas can be smoothly increased. Further, as the straight pipe section is installed, the combustion gas having an increased flow velocity can be rectified to further accelerate the combustion gas. For this reason, the erodent can efficiently collide with the test piece while the flow velocity of the combustion gas is sufficiently increased.

According to a fourth aspect of the present invention, in the erosion test apparatus, the combustor according to any one of the first to third aspects may include an air supply unit configured to supply air for temperature adjustment to a combustion gas.

According to the above-mentioned configuration, the air for temperature adjustment can be supplied to the combustion gas to decrease the temperature of the combustion gas. For this reason, as a supply amount of the air for temperature adjustment is increased or decreased, the temperature of the thermal barrier coating of the test piece can be easily adjusted to a desired temperature.

According to a fifth aspect of the present invention, in the erosion test apparatus, the accommodation support unit according to any one of the first to fourth aspects may include an observation window in communication with an accommodation space configured to accommodate the test piece.

According to the above-mentioned configuration, a state of the test piece during the erosion test can be observed via the observation window. For this reason, generation of deviation between a boundary condition of the test piece and a boundary condition of the real machine can be suppressed.

According to a sixth aspect of the present invention, an accelerator includes a tubular throttling section having a flow path cross-sectional area that gradually reduces downstream; and a straight pipe section extending in a straight pipe shape having a constant flow path cross-sectional area downstream from a downstream end section of the throttling section. An upstream end section of the throttling section is connected to a combustor configured to mix and combust compressed air and a fuel to obtain a combustion gas. A downstream end of the straight pipe section is connected to an accommodation support unit configured to accommodate and support a test piece having a front surface coated through thermal barrier coating.

According to the above-mentioned configuration, the flow velocity of the combustion gas of the combustor can be smoothly increased, and the combustion gas having the increased flow velocity can be rectified. For this reason, the erodent can efficiently collide with the test piece while the flow velocity of the combustion gas is sufficiently increased.

According to a seventh aspect of the present invention, an erosion test method includes supplying an erodent to a combustion gas obtained by mixing and combusting compressed air and a fuel, accelerating a flow velocity of the combustion gas including the erodent by gradually decreasing a flow path cross-sectional area, and then causing the combustion gas to collide with a test piece on which thermal barrier coating is performed.

According to the above-mentioned configuration, the erosion test can be performed under the same environment of the turbine member of the real machine using the apparatus sufficiently smaller than the real machine of the gas turbine. For this reason, evaluation of the thermal barrier coating can be easily and accurately performed.

Advantageous Effects of Invention

According to the erosion test apparatus, the accelerator and the erosion test method, the thermal barrier coating of the gas turbine using the combustion gas having a high temperature and a high flow velocity can be properly evaluated while suppressing an increase in size of the apparatus.

DETAILED DESCRIPTION OF THE INVENTION

Next, an erosion test apparatus, an accelerator and an erosion test method according to an embodiment of the present invention will be described with reference to the accompanying drawings.

Figure 1:
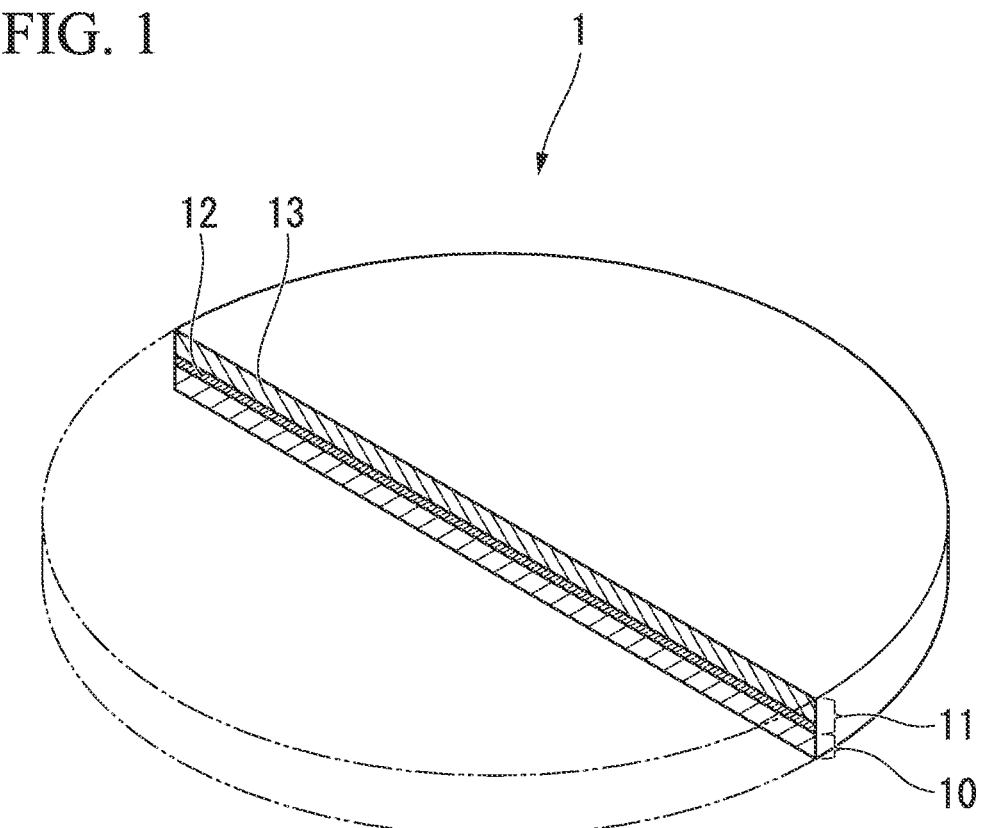
FIG. 1 is a partial cross-sectional perspective view of a test piece according to an embodiment of the present invention.

FIG. 1 is a partial cross-sectional perspective view of a test piece according to the embodiment of the present invention.

As shown in FIG. 1, a test piece 1 is formed by modeling a surface of a turbine blade of a gas turbine. The test piece 1 is constituted by a base material 10 and a thermal barrier coating layer 11. The test piece 1 according to the embodiment is formed in a disk shape.

The base material 10 is formed of a heat resistant alloy such as a Ni (nickel)-based alloy or the like.

The thermal barrier coating layer 11 is formed on a surface of the base material 10. The thermal barrier coating layer 11 includes a bond coating layer 12 and a top coating layer 13.

The bond coating layer 12 suppresses the top coating layer 13 from being exfoliated from the base material 10. The bond coating layer 12 is a metal bonded layer having good corrosion resistance and oxidation resistance. For example, the bond coating layer 12 is formed by thermally spraying a metal spray powder of a MCrAlY alloy serving as a flame coating material onto the surface of the base material 10. "M" of the MCrAlY alloy that constitutes the bond coating layer 12 represents a metal element. The metal element "M" is, for example, a single metal element or a combination of two or more elements, such as NiCo, Ni, Co, or the like.

The top coating layer 13 is deposited on the surface of the bond coating layer 12. The top coating layer 13 is formed by spraying a flame coating material including a ceramic onto the surface of the bond coating layer 12. The top coating layer 13 according to the embodiment is formed to have a porosity (an occupancy rate of pores per unit volume) of, for example, about 8 to 15%. A zirconia-based ceramic may be used as the flame coating material when the top coating layer 13 is formed. As the zirconia-based ceramic, yttria-stabilized zirconia (YSZ) and ytterbia-stabilized zirconia (YbSZ) or the like serving as zirconia ($ZrO_2$) partially stabilized by ytterbium oxide ($Yb_2O_3$) is provided. In the test piece 1 according to the embodiment, the thermal barrier coating layer 11 is disposed on a front surface thereof, and the base material 10 is disposed on a back surface thereof. That is, a metal that forms the base material 10 is exposed at the back surface side of the test piece 1. For example, a thickness of the base material 10 according to the embodiment may be equal to a thickness of the base material of the turbine blade of the gas turbine that is a real machine.

Figure 2:
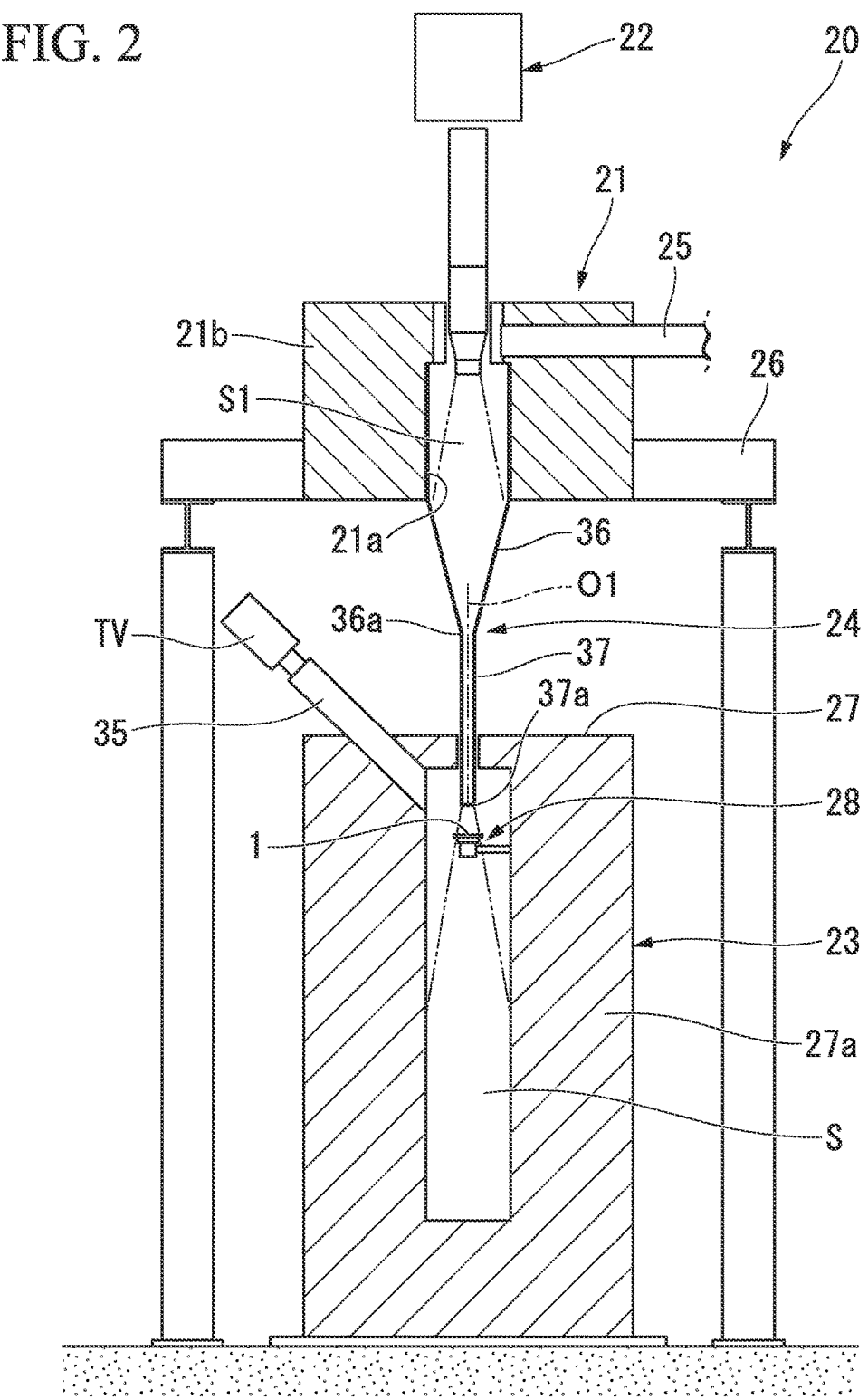
FIG. 2 is a partial cross-sectional view showing a configuration of an erosion test apparatus according to the embodiment of the present invention.

FIG. 2 is a partial cross-sectional view showing a configuration of an erosion test apparatus according to the embodiment of the present invention.

As shown in FIG. 2, an erosion test apparatus 20 includes a combustor 21, an erodent supply unit 22, an accommodation support unit 23 and an accelerator 24. The erosion test apparatus 20 is an apparatus for causing an erodent (powder) conveyed by a carrier gas to collide with the above-mentioned test piece 1. A user can evaluate erosion properties of the thermal barrier coating layer 11 by measuring abrasion loss of the test piece 1 tested by the erosion test apparatus 20.

The combustor 21 mixes a fuel with the compressed air compressed by a compressor (not shown) and combusts the mixed fuel. A combustion gas G combusted by the combustor 21 becomes a carrier gas of the erodent. The combustor 21 includes an air supply unit 25 that can supply the compressed air to the combustion gas G from the outside. The air supply unit 25 can finely adjust an air content supplied to the combustion gas G using an electromagnetic valve or the like. According to the air supply unit 25, for example, as the air content supplied to the combustion gas G is increased, a temperature of the combustion gas G can be decreased.

The combustor 21 is disposed over the accommodation support unit 23 by a frame 26. The combustor 21 is attached to the frame 26 by orienting an injection port 21a downward such that the combustion gas G is directed downward in a vertical direction. The combustor 21 includes a container 21b having good thermal insulation and thermal energy of the combustion gas G is suppressed from being discharged to the outside via the container 21b.

The erodent supply unit 22 supplies the erodent to the combustion gas G. The erodent supply unit 22 is attached to the combustor 21. The erodent supply unit 22 joins the erodent with the combustion gas G by quantitatively supplying the erodent accommodated in a hopper (not shown) or the like. For example, the erodent may be indirectly supplied to the combustion gas G by joining the erodent with the compressed air before combustion. For example, silica sand, alumina, fly ash, or the like, may be used as the erodent.

The accommodation support unit 23 accommodates the test piece 1 having a surface covered by the thermal barrier coating layer 11 in a state in which the test piece 1 is supported from below. The accommodation support unit 23 includes a chamber 27 and a support section main body 28.

The chamber 27 forms an accommodation space S configured to accommodate the test piece 1. Wall sections 29 that constitute the chamber 27 are formed of the same material having good thermal insulation as the container 21b of the above-mentioned combustor 21. That is, the chamber 27 can keep the accommodation space S warm through thermal insulation of the wall section 29. The wall section 29 and the container 21b guarantee the thermal insulation by forming the wall section 29 and the container 21b using a heat insulating material or attaching a heat insulating material to a framework (not shown).

Figure 3:
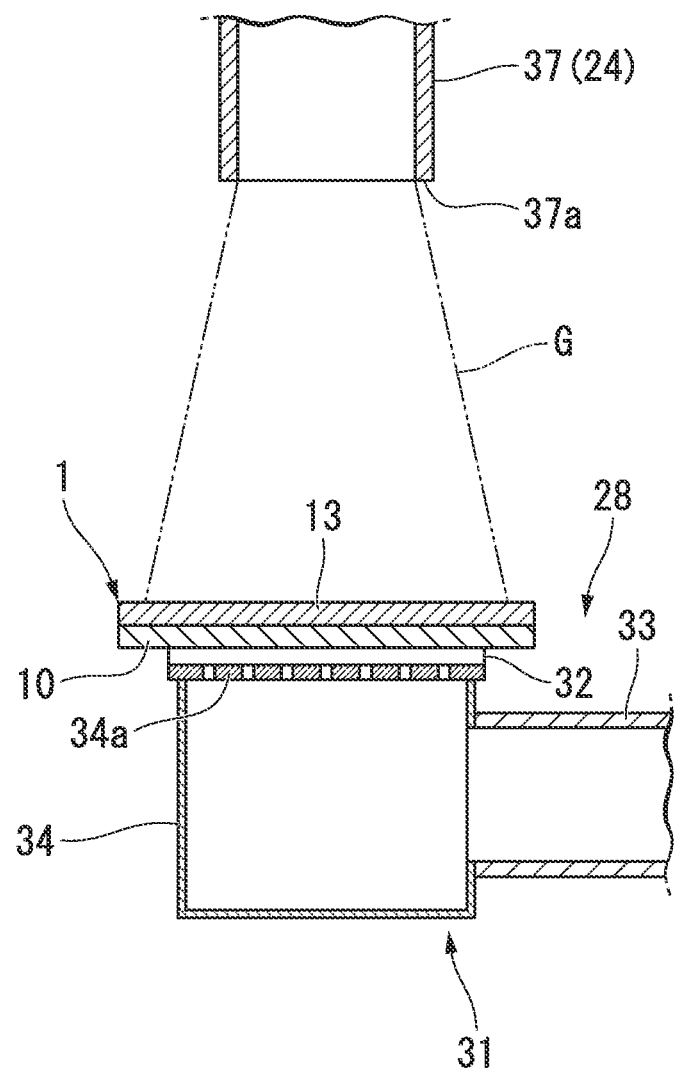
FIG. 3 is an enlarged cross-sectional view of a support section main body according to the embodiment of the present invention.

FIG. 3 is an enlarged cross-sectional view of the support section main body according to the embodiment of the present invention.

As shown in FIGS. 2 and 3, the support section main body 28 cools the base material 10 exposed to the back surface side of the test piece 1 while supporting the test piece 1 from below. The support section main body 28 includes a cooling air supply unit 31 and a support ring section 32.

The cooling air supply unit 31 blows the cooling air supplied from the outside against the base material 10. The cooling air supply unit 31 includes an air supply pipe 33 and a box body 34.

The air supply pipe 33 passes through a sidewall 27a (see FIG. 2) of the chamber 27. The air supply pipe 33 is formed in a tubular shape extending toward a center in a horizontal direction of the accommodation space S. The cooling air supplied from the outside toward the center of the accommodation space S flows through the air supply pipe 33. An end section of the air supply pipe 33 is connected to the sidewall of the box body 34.

The box body 34 changes a direction of the cooling air supplied by the air supply pipe 33 toward the back surface of the test piece 1 thereabove. In the box body 34 according to the embodiment, only an upper wall 34a is formed of a punching metal, a mesh, or the like, having a plurality of holes. Accordingly, the cooling air flowed into the box body 34 from the air supply pipe 33 is ejected upward via the holes of the upper wall 34a.

The support ring section 32 is formed in an annular shape protruding upward from an upper wall circumferential edge of the box body 34 of the cooling air supply unit 31. The test piece 1 is held by the support ring section 32. Bolt coupling, welding, or the like is used as a holding method of the test piece 1. Accordingly, the test piece 1 is supported by the support ring section 32 from below in a posture parallel to the upper wall 34a while the test piece 1 is spaced a predetermined distance from the upper wall 34a of the box body 34. The cooling air supply unit 31 may have a temperature detection unit such as a thermocouple or the like installed at a flow path through which the cooling air flows. As a result, a flow rate of the cooling air can be adjusted according to the temperature of the cooling air detected by the temperature detection unit to control temperature distribution in a thickness direction of the test piece 1.

The air supply pipe 33, the box body 34 and the support ring section 32 that constitute the above-mentioned support section main body 28 have not only a function as a conduit line configured to supply the cooling air but also a function as a cantilever beam configured to support the test piece 1 from below.

The accommodation support unit 23 includes an observation window section 35 in communication with the accommodation space S through which the test piece 1 is accommodated. The observation window section 35 extends in a radial direction about the test piece 1 supported by the support section main body 28. A Thermo Viewer TV that can detect the temperature distribution of the test piece 1 is attached to the observation window section 35 according to the embodiment. In the embodiment, the case in which only one observation window section 35 is formed at the accommodation support unit 23 is exemplarily shown. However, a plurality of observation window sections 35 may be formed with respect to the accommodation support unit 23. An observation apparatus other than the Thermo Viewer TV may be attached to the observation window section 35.

In FIG. 3, while not shown, the above-mentioned support ring section 32 includes, for example, a notch (not shown) or the like such that the cooling air that collides with the back surface of the test piece 1 is discharged to the accommodation space S. An erodent discharge mechanism (not shown) configured to discharge the erodent blown to the test piece 1 is installed at the accommodation support unit 23. The erodent blown to the test piece 1 is suctioned to be discharged to the outside of the chamber 27 by the erodent discharge mechanism.

The accelerator 24 accelerates a flow velocity of the combustion gas G including the erodent to cause the combustion gas G to collide with the test piece 1. As shown in FIG. 2, the accelerator 24 includes a throttling section 36 and a straight pipe section 37.

In the throttling section 36, an upstream end section in a direction in which the combustion gas G flows is connected to the combustor 21. The throttling section 36 is formed in a tubular shape in which a flow path cross-sectional area gradually reduces downstream in a direction in which the combustion gas G flows. In the throttling section 36 according to the embodiment, the flow path cross-sectional area is reduced at a constant inclination angle.

The straight pipe section 37 is formed in a straight pipe shape having a constant flow path cross-sectional area. The straight pipe section 37 connects a downstream end section 36a of the throttling section 36 and the accommodation support unit 23. More specifically, the straight pipe section 37 extends from the downstream end section 36a of the throttling section 36 to the inside of the accommodation space S of the accommodation support unit 23. A downstream end section 37a of the straight pipe section 37 is disposed immediately over the test piece 1. The straight pipe section 37 is disposed such that an axis O1 thereof is perpendicular to the front surface of the test piece 1 accommodated in the accommodation support unit 23. That is, the accelerator 24 brings an internal space S1 of the combustor 21 in communication with the accommodation space S of the accommodation support unit 23.

Figure 4:
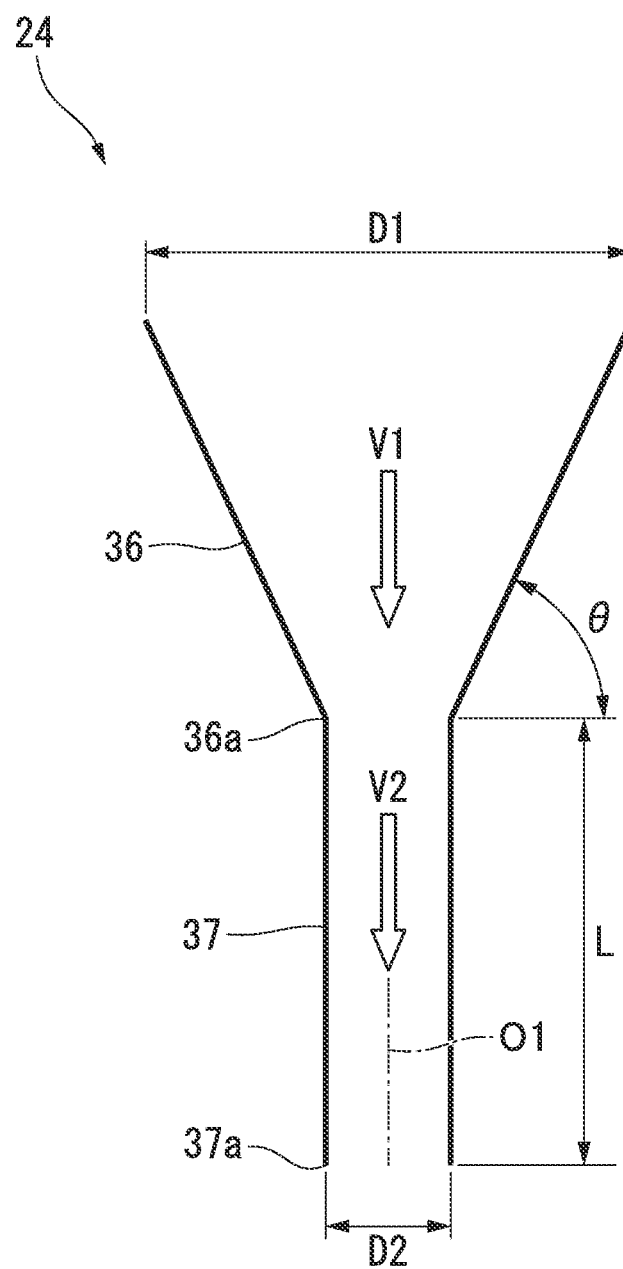
FIG. 4 is a view for describing an example of a shape of an accelerator according to the embodiment of the present invention.
Figure 5:
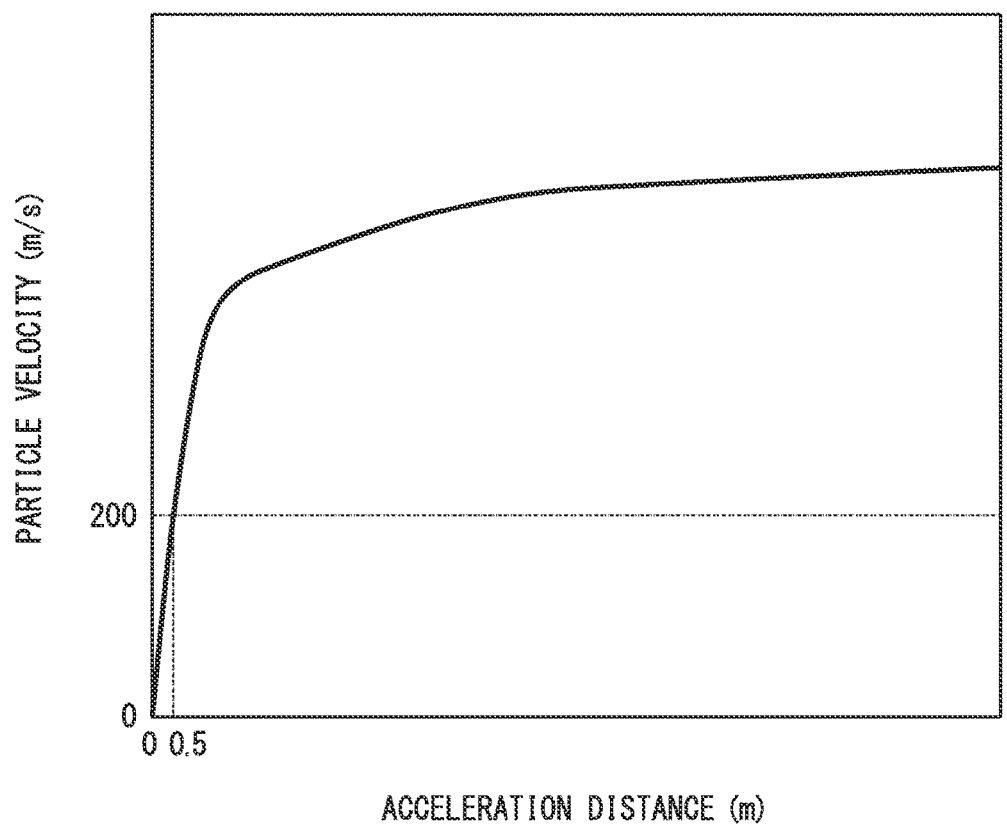
FIG. 5 is a graph in which a vertical axis represents a particle velocity (m/s) and a horizontal axis represents an acceleration distance (m).

FIG. 4 is a view for describing an example of a shape of the accelerator according to the embodiment of the present invention. FIG. 5 is a graph in which a vertical axis represents a particle velocity (m/s) and a horizontal axis represents an acceleration distance (m).

As shown in FIG. 4, an inclination angle θ of the throttling section 36 according to the embodiment is formed to be larger than a repose angle of the erodent. Here, the inclination angle θ is an angle with respect to a horizontal plane perpendicular to the axis O1.

An inner diameter D2 of the straight pipe section 37 is set to a large value such that a flow velocity in an outlet port of the straight pipe section 37 is smaller than a sonic velocity based on an amount of an exhaust gas of the combustor 21. For example, provided that the amount of the exhaust gas is "Q" (m³/s) and the sonic velocity of the exhaust gas is "Vc" (m/s) when a load of the combustor 21 is 100%, the inner diameter D2 can be obtained through the following equation (1).

$$D2 = (Q/Vc \times 4/\Pi)^{0.5} \quad (1)$$

The straight pipe section 37 is formed to have a length L such that a particle velocity of the erodent reaches a target value.

For example, in the case in which a gas flow velocity of the straight pipe section 37 is 600 m/s and a particle diameter of the erodent is 100 μm, as shown in FIG. 5, when a target value of the particle velocity of the erodent is set to 200 m/s, the length L (=acceleration distance) of the straight pipe section 37 is preferably about 0.5 m.

When a gas flow velocity of the throttling section 36 is "V1" and a gas flow velocity of the straight pipe section 37 is "V2," the following equation (2) is satisfied.

$$V1/V2 = D2/D1 \quad (2)$$

As shown in the graph of FIG. 5, in a range in which an acceleration distance approaches "0" (for example, a range of 0 to 1 m), the acceleration distance is increased to abruptly increase the particle velocity of the erodent. In other words, in the range in which the acceleration distance approaches "0," a rate of increase of the particle velocity is increased. However, in the vicinity in which the acceleration distance exceeds 1 m, the rate of increase of the particle velocity is abruptly decreased while deviation in the particle diameter occurs. In other words, when the acceleration distance exceeds 1 m, the particle velocity cannot be easily increased even when the acceleration distance is increased. That is, in the range of the acceleration distance in which the rate of increase of the particle velocity is high, as the length L of the straight pipe section 37 is set, the particle velocity can be efficiently increased while suppressing elongation of the straight pipe section 37.

Next, an erosion test method by the erosion test apparatus 20 according to the embodiment will be described.

First, the test piece 1 having the thermal barrier coating layer 11 is prepared on the front surface of the base material 10.

Further, the test piece 1 is set to the support section main body 28.

After that, the erodent having a desired particle diameter is previously accommodated in the hopper of the erodent supply unit 22.

Next, the erosion test apparatus 20 is driven. Then, the compressed air and the fuel are combusted in the combustor 21 in a mixed state, and the high temperature combustion gas G serving as a carrier gas is generated. Further, the compressed air is supplied to the high temperature combustion gas G via the air supply unit 25 to adjust the temperature thereof, and the erodent is quantitatively supplied.

The cooling air is blown from the back surface to the test piece 1 disposed in the accommodation space S of the accommodation support unit 23 via the cooling air supply unit 31. Accordingly, cooling of the base material 10 is continued.

In this state, the combustion gas G in which a certain amount of the erodent is contained flows into the accelerator 24 to be accelerated to a flow velocity at which the erodent reaches a target velocity. The erodent accelerated to the target velocity sequentially collides with the thermal barrier coating layer 11 of the test piece 1 held by the accommodation space S, more specifically, the top coating layer 13, via the accelerator 24. Here, the temperature adjustment of the combustion gas G and the temperature adjustment of the test piece 1 by the cooling air are performed such that the temperature distribution of the test piece 1 is observed through the Thermo Viewer TV by a user to become the same temperature distribution as that of the real machine.

After this state continues for a predetermined time, the user stops the erosion test apparatus 20, extracts the test piece 1 from the accommodation support unit 23, and evaluates an abrasion state or the like generated due to the top coating layer 13 or the like.

Accordingly, according to the above-mentioned embodiment, the combustion gas G of the combustor 21 can be used as the carrier gas of the erodent. For this reason, the temperature of the test piece 1 can be heated to the same temperature as the turbine member of the real machine. The combustion gas G including the erodent can collide with the test piece 1 after being accelerated by the accelerator 24. Accordingly, the flow velocity of the combustion gas G including the erodent can be increased to the same flow velocity as the combustion gas of the real machine using the compact combustor 21. That is, a boundary condition of the thermal barrier coating layer 11 of the test piece 1 can be equal to a boundary condition of the thermal barrier coating in the real machine. As a result, the erosion resistance of the thermal barrier coating layer 11 of the test piece 1 can be properly evaluated while suppressing an increase in size of the apparatus.

Further, as the cooling air supply unit 31 is provided, the base material 10 of the test piece 1 coated with the thermal barrier coating layer 11 can be cooled. For this reason, the same temperature distribution as the temperature distribution in the thickness direction of the turbine member of the real machine can be produced in the test piece 1. As a result, the erosion resistance of the test piece 1 with respect to the thermal barrier coating layer 11 can be more precisely evaluated.

Further, in the accelerator 24, as the flow path cross-sectional area of the throttling section 36 is gradually reduced, the flow velocity of the combustion gas can be smoothly increased. Further, as the straight pipe section 37 is installed, the combustion gas G having the flow velocity increased by the throttling section 36 can be rectified to further accelerate the combustion gas G. As a result, the erodent can efficiently collide with the test piece 1 while the flow velocity of the combustion gas G is sufficiently increased.

Further, air for temperature adjustment can be supplied to the combustion gas G to decrease the temperature of the combustion gas G. For this reason, as the supply amount of the air for temperature adjustment is increased or decreased, the temperature of the thermal barrier coating layer 11 of the test piece 1 can be easily adjusted to a desired temperature.

Further, a state of the test piece 1 during the erosion test can be observed via the observation window section 35. For this reason, generation of deviation between the boundary condition of the test piece 1 and the boundary condition of the real machine can be suppressed.

The present invention is not limited to the above-mentioned embodiment but various modifications may be added to the above-mentioned embodiment without departing from the spirit of the present invention. That is, specific shapes, configurations, or the like, provided in the embodiment are not limited to the examples but may be appropriately varied.

For example, in the above-mentioned embodiment, the case in which the support section main body 28 functions as the cooling unit configured to cool the test piece 1 has been described. However, the embodiment is not limited to the above-mentioned configuration but, for example, a mechanism configured to hold the test piece 1 and a mechanism configured to supply the cooling air may be separately installed.

Further, in the above-mentioned embodiment, the case in which the cooling air supply unit includes the air supply pipe 33 and the box body 34 has been described. However, the air supply pipe 33 may be curved such that the opening section of the air supply pipe 33 is directed toward the test piece 1, and the cooling air may be blown from the air supply pipe 33 to the test piece 1.

INDUSTRIAL APPLICABILITY

The present invention can be applied to the erosion test apparatus, the accelerator and the erosion test method, and the erosion resistance of the thermal barrier coating of the test piece can be properly evaluated while suppressing an increase in size of the apparatus.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

REFERENCE SIGNS LIST 1 test piece
10 base material
11 thermal barrier coating layer
12 bond coating layer
13 top coating layer
20 erosion test apparatus
21 combustor
21a injection port
21b container
22 erodent supply unit
23 accommodation support unit
24 accelerator
25 air supply unit
26 frame
27 chamber
27a sidewall
28 support section main body
29 wall section
31 cooling air supply unit
32 support ring section
33 air supply pipe
34 box body
34a upper wall
35 observation window section
36 throttling section
36a downstream end section
37 straight pipe section
37a downstream end section
S accommodation space
S1 internal space
G combustion gas
O1 axis
TV Thermo Viewer

What is claimed is:

1. An erosion test apparatus comprising:
   a combustor configured to mix and combust compressed air and a fuel to obtain a combustion gas;
   an erodent supply unit configured to supply an erodent to the combustion gas;
   an accommodation support unit configured to accommodate and support a test piece having a front surface coated through thermal barrier coating;
   an accelerator configured to accelerate the combustion gas including the erodent to collide with the test piece; and
   a cooling unit configured to blow a coolant to a back surface of the test piece to cool the test piece,
   wherein the accelerator comprises:
   a tubular throttling section connected to the combustor and having a flow path cross-sectional area that reduces downstream in a direction in which the combustion gas is to flow; and a straight pipe section extending in a straight pipe shape having a constant flow path cross-sectional area and connecting a downstream end section of the tubular throttling section and the accommodation support unit, wherein the straight pipe section extends from the downstream end section of the tubular throttling section to an inside of an accommodation space of the accommodation support unit, wherein a downstream end section of the straight pipe section is disposed immediately over the test piece, and wherein the combustor comprises an air supply unit configured to supply air for temperature adjustment to the combustion gas.

2. The erosion test apparatus according to claim 1, wherein the accommodation support unit comprises an observation window in communication with the accommodation space configured to accommodate the test piece.

3. An accelerator comprising:
a tubular throttling section having a flow path cross-sectional area that reduces downstream; and
a straight pipe section extending in a straight pipe shape having a constant flow path cross-sectional area downstream from a downstream end section of the tubular throttling section,
wherein an upstream end section of the tubular throttling section is connected to a combustor configured to mix and combust compressed air and a fuel to obtain a combustion gas,
wherein a downstream end of the straight pipe section is connected to an accommodation support unit configured to accommodate and support a test piece having a front surface coated through thermal barrier coating,
wherein the straight pipe section extends from the downstream end section of the tubular throttling section to an inside of an accommodation space of the accommodation support unit,
wherein a downstream end section of the straight pipe section is disposed immediately over the test piece, and
wherein an inclination angle of the tubular throttling section is larger than a repose angle of the erodent.

4. The accelerator according to claim 3, wherein a length of the straight pipe section has an acceleration distance in a range of 0 to 1 m.

5. An erosion test method comprising:
a first step of supplying an erodent to a combustion gas obtained by mixing and combusting compressed air and a fuel,
a second step in which cooling air is blown from a back surface to a test piece on which thermal barrier coating is performed via a cooling unit,
a third step of accelerating a flow velocity of the combustion gas including the erodent by decreasing a flow path cross-sectional area, and
a fourth step of causing the combustion gas including the erodent accelerated to collide by using an accelerator with the test piece on which the thermal barrier coating is performed,
wherein, in the third step, the combustion gas including the erodent is accelerated to a flow velocity at which the erodent reaches a target velocity, and
wherein, in the fourth step, the erodent accelerated to the target velocity sequentially collides with the test piece on which the thermal barrier coating is performed,
wherein the accelerator comprises:
a tubular throttling section having a flow path cross-sectional area that reduces downstream in a direction in which the combustion gas is to flow; and
a straight pipe section extending in a straight pipe shape having a constant flow path cross-sectional area and connecting a downstream end section of the tubular throttling section and an accommodation support unit configured to accommodate and support the test piece,
wherein the straight pipe section extends from the downstream end section of the tubular throttling section to an inside of an accommodation space of the accommodation support unit, and
wherein a downstream end section of the straight pipe section is disposed immediately over the test piece.

6. The erosion test method according to claim 5, wherein a target value of a particle velocity of the erodent is 200 m/s.

* * * * *